US005585056A

United States Patent [19]
Liu

[11] Patent Number: 5,585,056
[45] Date of Patent: Dec. 17, 1996

[54] PLASTICIZERS FOR FIBERS USED TO FORM SURGICAL DEVICES

[75] Inventor: Cheng-Kung Liu, Norwalk, Conn.

[73] Assignee: United States Surgical Corporation, Norwalk, Conn.

[21] Appl. No.: 433,099

[22] Filed: May 3, 1995

Related U.S. Application Data

[63] Continuation-in-part of Ser. No. 164,510, Dec. 9, 1993, abandoned, which is a continuation-in-part of Ser. No. 95,789, Jul. 21, 1993, abandoned.

[51] Int. Cl.⁶ .................................................... D01F 1/10
[52] U.S. Cl. ........................... 264/103; 29/433; 264/211; 264/238
[58] Field of Search .................................. 264/103, 129, 264/130, 210.6, 210.8, 211, 235.6, 238, 290.5; 29/433

[56] References Cited

U.S. PATENT DOCUMENTS

| | | |
|---|---|---|
| 3,186,961 | 6/1965 | Sears . |
| 3,297,033 | 1/1967 | Schmitt et al. . |
| 3,498,957 | 3/1970 | Jacobson . |
| 3,516,956 | 6/1970 | Reedy et al. . |
| 3,516,957 | 6/1970 | Gray, Jr. et al. . |
| 3,636,956 | 1/1972 | Schneider . |
| 3,792,010 | 2/1974 | Wasserman et al. . |
| 3,952,347 | 4/1976 | Comerford et al. . |
| 4,027,676 | 6/1977 | Mattei . |
| 4,052,988 | 10/1977 | Doddi et al. . |
| 4,185,637 | 1/1980 | Mattei . |
| 4,201,216 | 5/1980 | Mattei . |
| 4,353,839 | 10/1982 | Cleary et al. . |
| 4,532,929 | 8/1985 | Mattei et al. . |
| 4,544,694 | 10/1985 | Bower . |
| 4,605,730 | 8/1986 | Shalaby et al. . |
| 4,643,191 | 2/1987 | Bezwada et al. . |
| 4,653,497 | 3/1987 | Bezwada et al. . |
| 4,705,820 | 11/1987 | Wang . |
| 4,797,440 | 1/1989 | Schofield et al. . |
| 4,801,640 | 1/1989 | Dallmann et al. . |
| 4,838,267 | 6/1989 | Jamiolkowski et al. . |
| 4,839,215 | 6/1989 | Starling et al. . |
| 4,915,893 | 4/1990 | Gogolewski et al. . |
| 4,957,744 | 9/1990 | della Valle et al. . |
| 5,006,147 | 4/1991 | Thaler et al. . |
| 5,007,923 | 4/1991 | Bezwada et al. . |
| 5,019,093 | 5/1991 | Kaplan et al. . |
| 5,019,094 | 5/1991 | Bezwada et al. . |
| 5,032,638 | 7/1991 | Wang et al. . |
| 5,037,950 | 8/1991 | Bezwada et al. . |
| 5,047,048 | 9/1991 | Bezwada et al. . |
| 5,076,983 | 12/1991 | Loomis et al. . |
| 5,180,765 | 1/1993 | Sinclair . |

FOREIGN PATENT DOCUMENTS 1414600  11/1975  United Kingdom .

Primary Examiner—Leo B. Tentoni

[57] ABSTRACT

Filaments made from a mixture of absorbable polymers and plasticizers are used to make surgical articles. Preferred plasticizers used in the mixture are stearic acid and its salts.

20 Claims, 2 Drawing Sheets

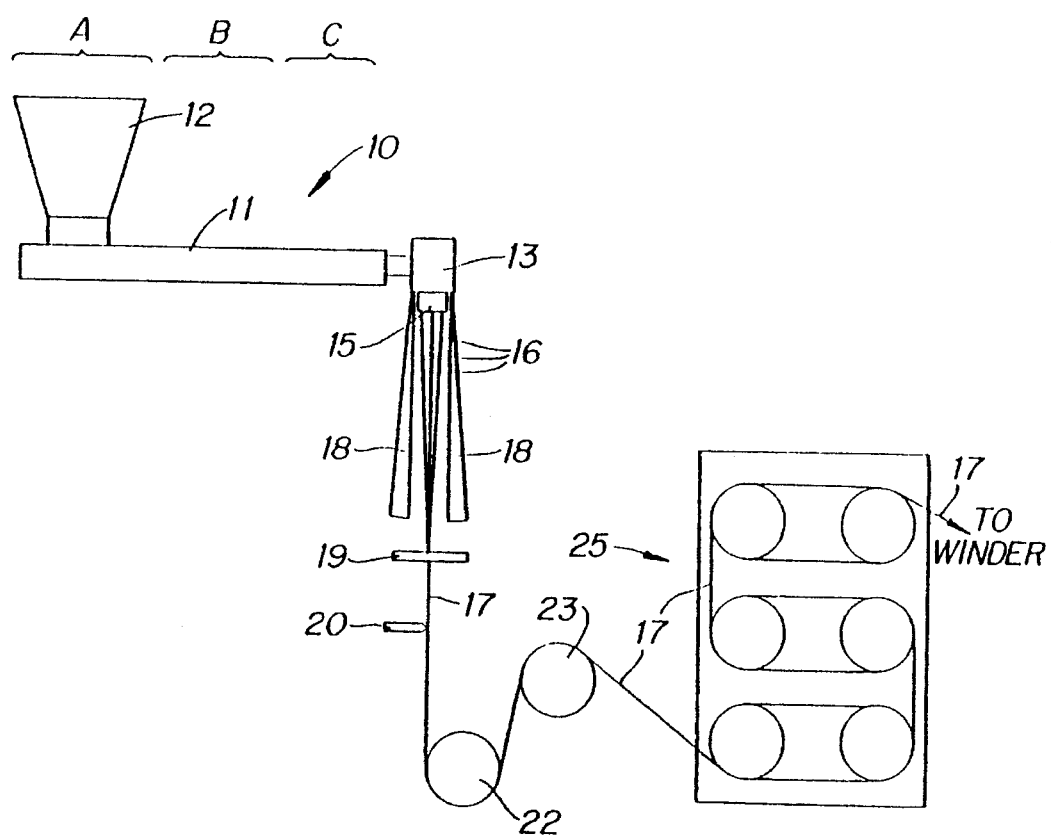

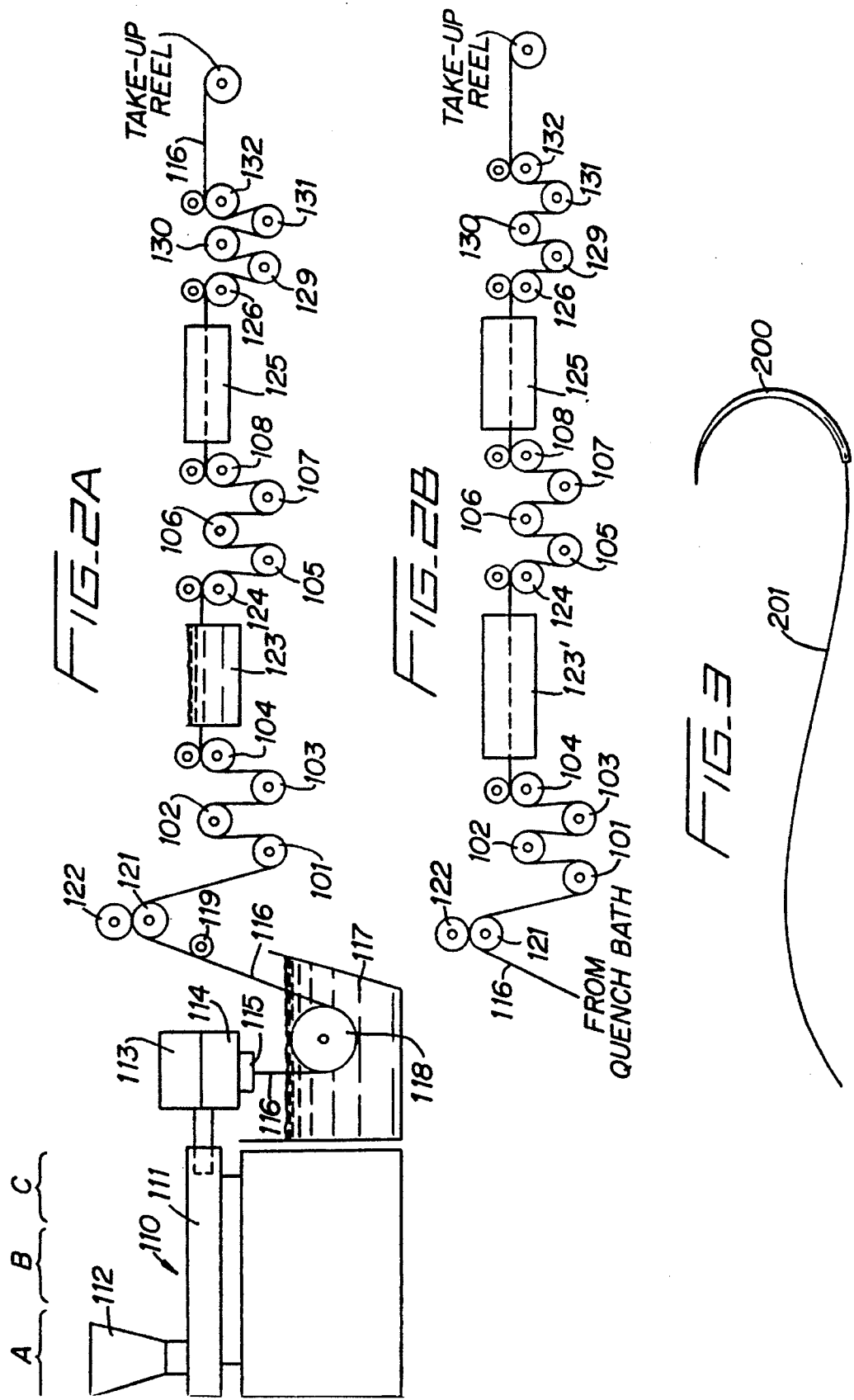

PLASTICIZERS FOR FIBERS USED TO FORM SURGICAL DEVICES

This application is a continuation-in-part application of U.S. Patent Application Ser. No. 08/164,510 filed Dec. 9, 1993, now abandoned which is a continuation-in-part application of U.S. Patent Application Ser. No. 08/095,789 filed Jul. 21, 1993, now abandoned.

FIELD OF THE INVENTION

The present invention relates generally to plasticizers for fibers. More specifically, this invention relates to plasticizer/polymer compositions to be formed into fibers, methods of preparing such fibers, and surgical devices made from such fibers.

BACKGROUND OF THE INVENTION

Plasticizers are molecules that when mixed with polar or hydrogen bonded polymers position themselves between the intermolecular bonds, thus increasing the spacing between adjacent bonds. In this manner, plasticizers lower the strength of the intermolecular forces, thus increasing the flexibility of the polymeric structure. For example, PVC, which is polar, is plasticized by substances such as dioctylphthlate. As another example, nylon, which is hydrogen bonded, is plasticized by water. Derivatives of long chain fatty aliphatic acids such as lauric, palmitic, stearic or behenic acid have been identified as spinning aids for polyamide fibers. (See, U.S. Pat. No. 3,516,956). Since the softening effect of plasticizers is equivalent to increasing extrusion temperatures, extruding plasticized polymers will require lower temperatures for comparable melt viscosities. Thus, the danger of thermal degradation of the polymer is generally decreased by employing a plasticizer. In this respect plasticizers are, indirectly, thermal stabilizes.

Absorbable surgical devices have been made from fibers of synthetic polymers such as polymer made from glycolide, lactide or p-dioxanone. With respect to polyglycolic acid sutures, U.S. Pat. No. 3,297,033 states at column 3, line 45 that: "In general, plasticizers tend to interfere with crystallinity, orientation, etc., and weaken fibers, but are useful for sponges and films." U.S. Pat. No. 3,792,010 describes plasticized polyester sutures prepared by reacting glycolide and lactide in the presence of a plasticizer such as bis-2-methoxyethyl phthalate or acetoxytriethyl citrate. U.S. Pat. No. 3,636,956 states at column 7, line 9 that any of a variety of plasticizers such as glyceryl triacetate, ethyl benzoate and diethyl phthalate can be used with polylactide and that preferred plasticizers for glycolide/lactide copolymers are dibutylphthalate and bis-2-methoxyethyl phthalate. U.S. Pat. No. 4,915,893 describes spinning polyesters such as polylactide with an additive such as a polyurethane, glycolide, lactide, camphor, benzoic acid-2-hydroxyacetate, hexamethylbenzene, 1,2-cyclohexandione and other low molecular weight organic compounds which are preferably soluble in trichlormethane and/or dichlormethane and ethanol and having a melting temperature in the range of 40° to 180° C.

SUMMARY OF THE INVENTION

It has now been found that fibers useful in making surgical devices can be prepared by extruding a composition containing an absorbable polymer and a plasticizer selected from the group consisting of stearic acid and its salts. Calcium stearate and stearic acid are particularly preferred plasticizers. In particularly useful embodiments the absorbable polymer is prepared from glycolide, glycolic acid, lactide, lactic acid and/or p-dioxanone.

BRIEF DESCRIPTION OF THE DRAWINGS

FIG. 1 is a schematic illustration of apparatus which is suitable for carrying out a preferred fiber manufacturing process in accordance with the present invention.

FIG. 2A is a schematic illustration of apparatus which is generally suitable for manufacturing monofilaments of larger size, e.g., size 2 to 2/0.

FIG. 2B is a modification of the apparatus of FIG. 2A which is generally preferred for the manufacture of monofilaments of smaller size, e.g. size 3/0 to 8/0.

FIG. 3 is a perspective view of a suture attached to a needle.

DESCRIPTION OF PREFERRED EMBODIMENTS

Fibers in accordance with the present invention are prepared by spinning or extruding a composition containing a bioabsorbable polymer and plasticizer.

The bioabsorbable polymer can be prepared from any of the monomers known to form biocompatible, bioabsorbable polymers, such as, for example, glycolide, glycolic acid, lactide, lactic acid, p-dioxanone, epsilon-caprolactone, alkylene carbonates and alkylene oxides. Polymers derived from glycolide, lactide, p-dioxanone or combinations thereof are preferred.

The plasticizers employed in this invention are selected from the group consisting of stearic acid and its salts. In particularly useful embodiments the plasticizer is stearic acid or calcium stearate.

In preparing filaments in accordance with the present invention, the absorbable polymer is in a granular, pellet or powder form. The polymer can be prepared in any manner and may, if necessary, be converted to the granular, pellet or powder form by any conventional means such as grinding, pulverizing, pelletizing or shredding. Polymerization techniques for preparing absorbable polymers are described for example in U.S. Patent Nos. 3,297,033; 4,052,988; 3,636,956; 4,605,730; 4,643,191; 4,653,497; 4,838,267; 5,007,923; 5,019,094; 5,047,048; and 5,037,950, the disclosures of which are incorporated herein by reference.

The absorbable polymer may be placed in a hopper and dried. An appropriate amount of plasticizer is then combined with the polymer and the polymer and plasticizer are mixed thoroughly to provide substantially uniform distribution of the plasticizer among the polymer particles or granules. The amount of plasticizer added may vary from about 0.001 to about 5 percent by weight based on the weight of the mixture. In particularly useful embodiments the amount of plasticizer employed is between about 0.01 to 2 percent by weight. Most preferably, the amount of plasticizer is between about 0.02 and 1 percent by weight.

The polymer and plasticizer can be mixed using any conventional technique, with or without heating. For example, a mechanical mixer, a static mixer or a combination of mixers may be employed to assist in providing a substantially uniform distribution of plasticizer and polymer. After mixing, the mixture is extruded or spun to form one or more filaments.

Known and conventional melt spinning apparatus can be used for the production of filaments, in accordance with this invention. FIG. 1 schematically illustrates a filament manufacturing operation in accordance with the invention. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polymeric resin to be spun into filaments are introduced to the extruder through hopper 12. Prior to being placed in hopper 12, the polymer is combined and mixed with the plasticizer.

Motor-driven metering pump 13 delivers the polymer/plasticizer mixture at a constant rate through spinneret 15 possessing one or more orifices of desired diameter to provide a plurality of molten filaments 16. While spinneret 15 is shown schematically in FIG. 1 as extruding three filaments, it should be understood that the spinneret may extrude anywhere from 1 to 200 filaments simultaneously.

The filaments 16 travel downward and are gathered together by guide 19 to produce a yarn 17. The distance the filaments 16 travel after emerging from spinneret 15 to the point where they contact guide 19, i.e., the air gap, can vary and can advantageously be from about 0.5 m to about 10 m and preferably from about 1 m to about 2 m. A chimney 18, or shield, can be provided to isolate filaments 16 from contact by air currents which might otherwise affect the cooling or movement of the filaments in some unpredictable manner. In general, the temperature of zones A, B and C of the barrel 11 will vary depending on a number of factors such as the chemical nature of the polymer, the size of the powder or pellets, the nature and amount of plasticizer employed, and the rate of feed.

Once filaments 16 are gathered together by guide 19 to produce yarn 17, a spin finish may be applied to yarn 17. The spin finish is preferably applied to "as spun" filaments (i.e., to filaments which have not been drawn or otherwise treated, physically or chemically) which have been gathered into a yarn 17. The spin finish can be any desired spin finish composition and can be applied using any known technique. As seen in FIG. 1, the yarn 17 may be passed along the edge of applicator 20 to which the spin finished is supplied at a predetermined rate.

The yarn can be processed in any manner after the application of the spin finish. The spin finish will assist in holding the individual filaments together, thereby preventing entanglement or separation of the filaments during subsequent processing. The spin finish also provides lubrication between the yarn and any rollers or godets employed in subsequent processing. In addition, the spin finish will function as a heat transfer medium during subsequent processing, such as drawing, to provide more uniform heating of the yarn than can be achieved by simply passing the yarn through heated godets or heated air.

An example of subsequent processing is shown in FIG. 1. After application of the spin finish, the yarn may be wrapped around a lube godet 22 and one or more additional godets, for example, godet 23, to take up and adjust the tension on the yarn. The yarn 17 may then be passed to a heated draw frame 25. Draw frame 25 may be of any configuration. As shown in FIG. 1, draw frame 25 includes three pairs of godets which can be used to stretch the yarn or to allow relaxation and perhaps shrinkage of yarn 17. The speed at which the godets rotate and the temperature at which the draw frame is maintained will determine the amount of stretching and/or relaxation which occurs. Setting the various speeds and temperatures to achieve a desired result is within the purview of those skilled in the art.

Table I provides ranges of values for spinning and stretching parameters suitable for producing yarns from a composition containing a copolymer of glycolide and lactide and a plasticizer in accordance with the present invention.

TABLE I

MELT SPINNING APPARATUS AND OPERATING CONDITIONS

| Apparatus Component, Operating Parameter | Copolymer of Glycolide and Lactide and Plasticizer |
|---|---|
| Extruder barrel temp., zone A, °C. | 200–240 |
| Extruder barrel temp., zone B, °C. | 210–250 |
| Extruder barrel temp., zone C, °C. | 210–250 |
| Extruder barrel pressure, psi | 700–1500 |
| Extruder barrel melt temp., °C. | 210–260 |
| Pump size, cc per rev. | 16–.584 |
| Pump rpm | 10–40 for size .16 pump 3–11 size .584 pump |
| Pump temp., °C. | 190–250 |
| Pump pressure, psi | 500–1500 |
| Pump melt temp., °C. | 190–250 |
| Block temp., °C. | 200–250 |
| Clamp temp., °C. | 200–250 |
| Adapter temp., °C. | 200–250 |
| Candle filter, screen, microns | 10–60 |
| No. of spinneret orifices | 5–200 |
| Diameter of spinneret orifices, .001 in | 5–30 |
| Spinneret temp., °C. | 190–250 |
| Spinneret pressure, psi | 500–2500 |
| Spinneret melt temp., °C. | 190–250 |
| cc/hr output, per spinneret orifice | 1–80 |
| First pair of godets, °C. | 50–90 |
| First pair of godets, mpm | 80–200 |
| Second pair of godets, °C. | 60–120 |
| Second pair of godets, mpm | 300–1200 |
| Draw (stretch) ratio | 2–8 |
| Third pair of godets, °C. | ambient |
| Third pair of godets, mpm | 250–1150 |
| Shrinkage (relaxation), percent | 3–10 |

After drawing, the yarn may then be sent to a winder where it can be placed onto spools for storage while awaiting further treatment or use.

The yarn may be formed into a surgical device using any known technique such as braiding, knitting, weaving, air-entangling, twisting, tying, winding, or forming a composite using the yarn or pieces thereof as a reinforcing component.

EXAMPLES

The following Examples 1 and 2 show the preparation of a yarn from 27 filaments made from a poly(glycolide-co-lactide) (92.5:7.5 molar ratio; inherent viscosity 1.3–1.45 dl/g) plasticized with calcium stearate (Example 1) and stearic acid (Example 2). For comparison purposes, a control yarn of the same absorbable copolymer made by the same process but containing no plasticizer were also prepared. The spinning conditions for preparing the yarns of the Examples and the control are given in Table 2.

TABLE 2

|  | CONTROL | EXAMPLE 1 | EXAMPLE 2 |
|---|---|---|---|
| Resin Drying Conditions | 10 hours at 100° C. | 10 hours at 100° C. | 10 hours at 100° C. |
| Additive | None | Calcium stearate | Stearic Acid |
| Drying Conditions for additive | None | 12 hours at 120° C. | 12 hours at 45° C. |
| Percent of Additive | 0.000 | 0.050 | 0.100 |
| Spin Finish | 20% Lurol in Iso-propanol | | |
| Die | 32 Holes | 32 Holes | 32 Holes |
| Pump c.c./rev | 0.16 | 0.16 | 0.16 |
| Filter (micron) | 20 | 20 | 20 |

TABLE 2-continued

|  |  | CONTROL | EXAMPLE 1 | EXAMPLE 2 |
| --- | --- | --- | --- | --- |
| Barrel 1 | (°C.) | 218 | 215 | 210 |
| Barrel 2 | (°C.) | 222 | 218 | 218 |
| Barrel 3 | (°C.) | 222 | 218 | 218 |
| Clamp 1 | (°C.) | 214 | 212 | 212 |
| Mixer | (°C.) | 214 | 212 | 212 |
| Clamp 2 | (°C.) | 214 | 212 | 212 |
| Adaptor | (°C.) | 210 | 210 | 210 |
| Block | (°C.) | 210 | 210 | 210 |
| Pump | (°C.) | 210 | 210 | 210 |
| Die | (°C.) | 212 | 210 | 214 |
| Chimney | (°C.) | 100 | 100 | 100 |
| Chimney Air | (°C.) | 109 | 110 | 110 |
| Barrel Melt | (°C.) | 218 | 215 | 215 |
| Pump Melt | (°C.) | 211 | 205 | 205 |
| Die Melt | (°C.) | 219 | 216 | 215 |
| Screw RPM |  | 1.8 | 8.5 | 8.4 |
| Pump RPM |  | 19.4 | 19.4 | 20.25 |
| Lube Pump | (ml/m) | 0.20 | 0.20 | 0.20 |

TABLE 2-continued

|  |  | CONTROL | EXAMPLE 1 | EXAMPLE 2 |
| --- | --- | --- | --- | --- |
| Lube Godet | (mpm) | 133 | 134 | 134 |
| Godet 1 | (mpm) | 137 | 138 | 136 |
| Godet 2 | (mpm) | 767 | 769 | 772 |
| Godet 3 | (mpm) | 750 | 751 | 750 |
| Barrel | (psi) | 970 | 929 | 835 |
| Pump | (psi) | 1000 | 1000 | 1000 |
| Die | (psi) | 577 | 710 | 758 |
| Average Denier |  | 43.7 | 44.2 | 43.1 |
| Average Tenacity |  | 6.6 | 7.1 | 7.2 |
| Average Elongation |  | 21 | 20 | 21 |

The yarn was drawn 5.5 times and then twisted, combined and twisted again to form a cable-like suture. The cable was then annealed, post-washed and post-treated to remove any residual monomer or other vaporizable impurities. The processing of each of the yarns was essentially in accordance with the process described in U.S. Pat. No. 5,019,093 and U.S. Patent Application Ser. No. 07/855,682, the disclosures of which are incorporated herein by reference. The physical properties of the yarns were tested using the following procedures:

| PROCEDURES FOR MEASURING PHYSICAL PROPERTIES | |
| --- | --- |
| Physical Property | Test Procedure |
| knot-pull strength, kg | U.S.P. XXI, <881> tensile strength, surgical suture |
| straight-pull strength, kg | ASTM D2256-88 |
| elongation at break, % | ASTM D2256-88 |
| tensile strength, $kg/mm^2$ | ASTM D2256-88, Instron Corporation Model No. 1122 |
| Tenacity | ASTM D2256-88 |
| In Vitro Strength Retention | To simulate in vivo conditons, the suture samples were stored in a container filled with Sorenson's buffer solution at 37° C. After various period of time, the suture samples were then removed from the container to test their knot-pull strength, using an Instron tensile tester. In vitro knot-pull strength retention is indicative of in vivo strength retention. |

The physical properties of suture fabricated from the control yarn and sutures made with plasticized filaments in accordance with this invention are presented in Table 3.

TABLE 3

|  | Plasticizer | Denier | Diameter (laser) | Straight-Pull Strength | Elongation at Break | Knot Pull Strength | Fiber Tenacity | In Vitro Strength rerention after 3 weeks |
| --- | --- | --- | --- | --- | --- | --- | --- | --- |
| Example 1 | Calcium Stearate | 950 | 360 mm | 6.38 kg. | 18.9% | 3.54 kg | 7.1 g/d | 55% |
| Example 2 | Stearic Acid | 975 | .354 mm | 5.97 kg. | 16.7% | 3.66 kg | 7.2 g/d | 49% |
| Control | None | 963 | .347 mm | 6.06 kg. | 18.9% | 3.31 kg. | 6.6 g/d | 44% |

Monofilaments, rather than multifilament yarn, also can be formed in accordance with this invention. The monofilament may be used as sutures, or combined with other monofilaments to form a surgical article.

A suitable process for the manufacture of monofilament sutures of the present invention comprises the operations of melt extruding a mixture of resin and plasticizer at an extrusion temperature of from about 170° C. to about 250° C. to provide a monofilament, stretching the solidified monofilament at a temperature of from about 20° C. to about 90° C. in water (or other suitable liquid medium) or at from about 30° C. to about 140° C. in air (or other suitable gaseous medium) at a stretch ratio of from about 3:1 to about 10:1 to provide a stretched monofilament. Optionally, the stretched monofilament may be stretched again in air or other suitable gaseous medium preferably at about 130° C. Preferably, the monofilament is then frozen at a temperature of from about −15° C. to about 0° C. The suture may then be annealed at a temperature of from about 50° C. to about 130° C. to provide the finished suture.

FIG. 2A schematically illustrates a monofilament suture manufacturing operation which is especially suitable for producing larger size sutures, e.g., those of sizes 2/0 and larger. Extruder unit 110 is of a known or conventional type and is equipped with controls for regulating the temperature of barrel 111 in various zones thereof, e.g., progressively higher temperatures in three consecutive zones A, B and C along the length of the barrel. Pellets or powder of resins mixed with a plasticizer in accordance with the present invention are introduced to the extruder through hopper 112.

Motor-driven metering pump 113 delivers melt extruded resin mixture at a constant rate to spin pack 114 and thereafter through spinneret 115 possessing one or more orifices of desired diameter to provide a molten monofilament 116 which then enters quench bath 117, e.g., containing water, where the monofilament solidifies. The distance monofilament 116 travels after emerging from spinneret 115 to the point where it enters quench bath 117, i.e., the air gap, can vary and can advantageously be from about 0.5 to about 100 cm and preferably from about 1 to about 20 cm. If desired, a chimney (not shown), or shield, can be provided to isolate monofilament 116 from contact with air currents which might otherwise affect the cooling of the monofilament in an unpredictable manner. In general, barrel zone A of the extruder can be maintained at a temperature of from about 100° C. to 220° C., zone B at from about 160° C. to 230° C. and zone C at from about 170° C. to about 240° C. Additional temperature parameters include: metering pump block 113 at from about 170° C. to about 230° C., spin pack 114 at from about 170° C. to about 230° C., spinneret 115 at from about 170° C. to about 230° C. and quench bath at from about 10° C. to about 80° C.

Monofilament 116 is passed through quench bath 117 around driven roller 118 and over idle roller 119. Optionally, a wiper (not shown) may remove excess water from the monofilament as it is removed from quench bath 117. On exiting the quench bath the monofilament is wrapped around a first godet 121 provided with nip roll 122 to prevent slippage which might otherwise result from the subsequent stretching operation; and subsequently wrapped around godets 101, 102, 103 and 104 or any other suitable godet arrangement. Monofilament 116 passing from godet 104 is stretched, e.g., with stretch ratios on the order of from about 3:1 to about 10:1 and preferably from about 4:1 to about 7:1, to effect its orientation and thereby increase its tensile strength.

In the stretching operation shown in FIG. 2A, generally suitable for larger size sutures, e.g., sizes 2 to 2/0, monofilament 116 is drawn through hot water (or other suitable liquid medium) draw bath 123 by means of godets 124, 105, 106, 107 and 108 or any other suitable arrangement of godets which rotate at a higher speed than godet 104 to provide the desired stretch ratio. The temperature of hot water draw bath 123 is advantageously from about 30° C. to about 90° C. and preferably is from about 30° C. to about 50° C.

In the alternative stretching operation shown in FIG. 2B, generally preferred for smaller sutures sizes, e.g., sizes 3/0 to 8/0, monofilament 116 is drawn by godets 124, 105, 106, 107, and 108 or any other suitable godet arrangement through hot air convection oven chamber 123' at a temperature of from about 30° C. to about 140° C. and preferably from about 50° C. to about 130° C. to provide the desired amount of stretch. Following the stretching operation shown in FIG. 2A or 2B, monofilament 116 optionally may be subjected to an on-line annealing and/or additional stretching without shrinkage or relaxation with shrinkage operation as a result of which the monofilament shrinks. In the processes of FIGS. 2A and 2B, on line annealing with or without relaxation when desired is accomplished by driving monofilament 116 by godets 126, 129, 130, 131, and 132 or any other suitable godet arrangement through second hot air oven chamber 125 at a temperature of from about 40° C. to about 150° C. and preferably from about 60° C. to about 130° C. During the relaxation process, at these temperatures, monofilament 116 will generally recover to within about 80 to about 97 percent, and preferably to within about 95 percent, of its pre-annealed length to provide the finished suture. For relaxation, the third godet rotates at a slower speed than the second godet thus relieving tension on the filament.

Annealing of the suture also may be accomplished without shrinkage of the suture. In carrying out the annealing operation, the desired length of suture may be wound around a creel and the creel placed in a heating cabinet maintained at the desired temperature, e.g. about 60° C. to about 130° C., as described in U.S. Pat. No. 3,630,205. After a suitable period of residency in the heating cabinet, e.g., about 18 hours or so, the suture will have undergone essentially no shrinkage. As shown in U.S. Pat. No. 3,630,205, the creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

The suture of the present invention, suture 201, may be attached to a surgical needle 200 as shown in FIG. 3 by methods well known in the art. Wounds may be sutured by passing the needled suture through tissue to create wound closure. The needle preferably is then removed from the suture and the suture tied.

EXAMPLE 3

A monofilament is made from a copolymer of glycolide and lactide containing about 18 weight percent glycolide and about 82 weight percent lactide. The production of the copolymer is described in U.S. Patent No, the disclosure of which is incorporated herein by reference. The resin is mixed with 3% by weight of calcium stearate and extruded into monofilaments of size using the following conditions:

| CONDITIONS OF MANUFACTURING PLASTICIZED MONOFILAMENT | |
|---|---|
| Process Conditions | |
| | Extrusion Operation |
| extruder screw, rpm | 2.2 |
| pump rpm | 12.7 |
| driven roller, mpm | 2.7 |
| barrel temp., °C., zone A | 115 |
| barrel temp., °C., zone B | 180 |
| barrel temp., °C., zone C | 183 |
| clamp temp., °C. | 182 |
| adapter temp., °C. | 183 |
| pump temp., °C. | 183 |
| barrel melt temp., °C. | 177 |
| pump melt temp., °C. | 179 |
| Spinneret melt temp., °C. | 180 |
| barrel pressure, psi | 1040 |
| pump pressure, psi | 500 |
| pump size, cc per revolution | 0.16 |
| diameter of spinneret orifices, mm | 1.25 |
| no. of spinneret orifices | 1 |
| quench bath temp., °C. | 18 |
| depth of driven roller, cm | 19 |
| | Stretching Orienting Operation |
| first draw oven temp, °C. | 126 |
| first godet station, mpm | 4.0 |
| second godet station, mpm | 22.4 |

-continued

CONDITIONS OF MANUFACTURING PLASTICIZED MONOFILAMENT

| Process Conditions | |
|---|---|
| second oven temp., °C. | 130 |
| third godet station, mpm | 29.5 |
| draw ratio | 7.4:1 |

For comparison purposes, a control monofilament was prepared using the same copolymer and the same extrusion and stretching conditions, however, the control monofilament was made without plasticizer. Both monofilaments were annealed at 90° C. for 18 hours in a nitrogen oven.

The physical properties of the monofilament of Example 3 prepared in accordance with the present invention and the control monofilament are presented in Table 4.

TABLE 4

| | Knot-Pull (kpsi) | Straight Pull (kpsi) |
|---|---|---|
| Example 3 | 40 | 62 |
| Control | 34 | 60 |

As the data presented in Table 4 shows, the monofilament of Example 3 exhibited both higher knot-pull and straight-pull tensile strength compared to the control monofilament.

Obviously, other modifications and variations of the present invention are possible in light of the above teachings. For example, multifilament yarns may be formed rather than monofilaments. The monofilaments may be used as sutures, or combined with other monofilaments to form a surgical article. It is therefore to be understood that changes may be made in particular embodiments of the invention described which changes are within the full intended scope of the invention as defined by the claims.

What is claimed is:

1. A method of making a surgical article comprising:
   a. providing a mixture comprising an absorbable polymer and a plasticizer selected from the group consisting of stearic acid and its salts;
   b. forming at least one filament from said mixture; and
   c. forming a surgical article from said at least one filament.

2. A method of making a surgical article comprising:
   a. providing a mixture comprising an absorbable polymer and a plasticizer selected from the group consisting of stearic acid and calcium stearate;
   b. forming at least one filament from said mixture; and
   c. forming a surgical article from said at least one filament.

3. A method as in claim 1 wherein said absorbable polymer is selected from the group consisting of polymers made from one or more of glycolide, glycolic acid, lactide, lactic acid, epsilon-caprolactone and p-dioxanone.

4. A method as in claim 1 wherein said absorbable polymer is a copolymer of glycolide and lactide.

5. A method as in claim 1 wherein said absorbable polymer comprises repeating units of p-dioxanone.

6. A method as in claim 5 wherein said absorbable polymer is a homopolymer of p-dioxanone.

7. A method as in claim 5 wherein said absorbable polymer is a copolymer containing repeating units of p-dioxanone.

8. A method as in claim 7 wherein said copolymer is a block copolymer.

9. A method as in claim 1 wherein said plasticizer is calcium stearate.

10. A method as in claim 1 wherein said step of providing a mixture comprises:
    a. providing particles of absorbable polymer;
    b. combining said plasticizer with said particles; and
    c. mixing the particles and plasticizer together to provide a substantially uniform distribution of plasticizer among the particles.

11. A method as in claim 1, wherein the step of forming at least one filament comprises melt spinning the mixture.

12. A method as in claim 1, wherein the step of forming a surgical article comprises attaching a surgical needle to a single filament.

13. A method as in claim 1, wherein a plurality of filaments are formed in the step of forming at least one filament from the mixture.

14. A method as in claim 13, wherein the step of forming a surgical article comprises gathering the plurality of filaments to form a yarn.

15. A method as in claim 13, wherein the step of forming a surgical article comprises attaching a needle to the plurality of filaments.

16. A method as in claim 1, wherein the mixture contains from about 0.001 to about 5 percent of the plasticizer based on the weight of the mixture.

17. A method as in claim 1, wherein the mixture contains from about 0.02 to about 1 percent of the plasticizer based on the weight of the mixture.

18. A method making a surgical article comprising:
    a. providing a mixture containing an absorbable polymer and a plasticizer selected from the group consisting of stearic acid and calcium stearate;
    b. extruding the mixture to form a filament; and
    c. forming a surgical article from the filament.

19. A method as in claim 18 wherein the step of extruding the mixture comprises melt spinning the mixture to form a filament.

20. A method as in claim 18 wherein a plurality of filaments are formed from the mixture in the extruding step.

* * * * *